United States Patent
Zhang et al.

(10) Patent No.: US 12,097,245 B2
(45) Date of Patent: Sep. 24, 2024

(54) HYPOGLYCEMIC PHARMACEUTICAL COMPOSITION

(71) Applicant: Jing Zhang, Jiangsu (CN)

(72) Inventors: Jing Zhang, Jiangsu (CN); Wenbo Jin, Jiangsu (CN)

(73) Assignee: Jing Zhang, Jiangsu (CN)

( * ) Notice: Subject to any disclaimer, the term of this patent is extended or adjusted under 35 U.S.C. 154(b) by 667 days.

(21) Appl. No.: 17/282,831

(22) PCT Filed: May 6, 2020

(86) PCT No.: PCT/CN2020/088645
§ 371 (c)(1),
(2) Date: Apr. 5, 2021

(87) PCT Pub. No.: WO2020/248741
PCT Pub. Date: Dec. 17, 2020

(65) Prior Publication Data
US 2021/0353718 A1 Nov. 18, 2021

(30) Foreign Application Priority Data
Jun. 10, 2019 (CN) .......................... 201910498353.1

(51) Int. Cl.
*A61K 38/26* (2006.01)
*A61K 9/00* (2006.01)
(Continued)

(52) U.S. Cl.
CPC .......... *A61K 38/26* (2013.01); *A61K 9/0053* (2013.01); *A61K 47/12* (2013.01); *A61K 47/20* (2013.01);
(Continued)

(58) Field of Classification Search
CPC ........ A61K 47/20; A61K 47/32; A61K 47/36; A61K 31/194; A61K 31/198; A61K 38/26;
(Continued)

(56) References Cited

U.S. PATENT DOCUMENTS

| | | |
|---|---|---|
| 8,399,011 B1 | 3/2013 | Wong et al. |
| 2009/0011008 A1 | 1/2009 | Sung et al. |

(Continued)

FOREIGN PATENT DOCUMENTS

| | | |
|---|---|---|
| CN | 102000325 A | 4/2011 |
| CN | 102100912 A | 6/2011 |

(Continued)

OTHER PUBLICATIONS

Rowe et al., Handbook of Pharmaceutical Excipients, 6th Ed., 917 pages, Published by Pharmaceutical Press 2009, excerpt of title pages, table of contents and pp. 110-114, 159-161, 640-642, and 651-653 (Year: 2009).*

(Continued)

*Primary Examiner* — Randall L Beane
(74) *Attorney, Agent, or Firm* — HAUPTMAN HAM, LLP (57) ABSTRACT

A pharmaceutical composition having a hypoglycemic effect, comprising: a GLP-1 receptor agonist, and a composition for promoting small-intestinal absorption; wherein the composition for promoting small-intestinal absorption comprises sodium lauryl sulfate, carbomer, chitosan, and sodium citrate. The composition for promoting small intestinal absorption according to the present invention may be prepared into a composite adjuvant, which, when combined with a GLP-1 agonist, can improve the absorption of this active ingredient in the small intestine and the like.

7 Claims, 3 Drawing Sheets

(51) Int. Cl.
  *A61K 47/12* (2006.01)
  *A61K 47/20* (2006.01)
  *A61K 47/32* (2006.01)
  *A61K 47/36* (2006.01)
  *A61P 3/10* (2006.01)

(52) U.S. Cl.
  CPC .............. *A61K 47/32* (2013.01); *A61K 47/36* (2013.01); *A61P 3/10* (2018.01)

(58) Field of Classification Search
  CPC ...... A61K 47/12; A61K 9/0053; A61K 9/145; A61K 9/146; A61K 9/19; A61K 9/4858; A61K 9/4866; A61K 9/4891; A61P 3/10; A61P 43/00
  See application file for complete search history.

(56) References Cited

U.S. PATENT DOCUMENTS

2017/0304195 A1* 10/2017 Föger ................... A61K 47/18
2018/0271792 A1*  9/2018 Mantripragada ...... A61K 47/60

FOREIGN PATENT DOCUMENTS

| CN | 104740647 A | 7/2015 | |
|---|---|---|---|
| CN | 106661096 A | 5/2017 | |
| CN | 106794252 A | 5/2017 | |
| CN | 108135962 A | 6/2018 | |
| CN | 109498559 A | 3/2019 | |
| EP | 3275460 A1 | 1/2018 | |
| WO | WO-2006054307 A2 * | 5/2006 | ........... A61K 31/401 |
| WO | WO-2016055550 A1 * | 4/2016 | ............ A61K 38/08 |
| WO | WO-2017060500 A1 * | 4/2017 | ............ A61K 33/26 |
| WO | 2018175250 A1 | 9/2018 | |

OTHER PUBLICATIONS

Maher et al., Intestinal permeation enhancers for oral peptide delivery. Adv Drug Deliv Rev. Nov. 15, 2016;106(Pt B):277-319. doi: 10.1016/j.addr.2016.06.005. Epub Jun. 16, 2016. PMID: 27320643 (Year: 2016).*

Thanou et. al., Oral drug absorption enhancement by chitosan and its derivatives. Adv Drug Deliv Rev. Nov. 5, 2001;52(2):117-26. doi: 10.1016/s0169-409x(01)00231-9. PMID: 11718935 (Year: 2001).*

Welling et al., The role of citric acid in oral peptide and protein formulations: relationship between calcium chelation and proteolysis inhibition. Eur J Pharm Biopharm. Apr. 2014;86(3):544-51. doi: 10.1016/j.ejpb.2013.12.017. Epub Dec. 31, 2013. PMID: 24384069 (Year: 2013).*

International Search Report in the international application No. PCT/CN2020/088645, mailed on Aug. 13, 2020.

Written Opinion of the International Searching Authority in the international application No. PCT/CN2020/088645, mailed on Jul. 31, 2020 and English translation provided by Google Translate.

First Office Action and search report for Chinese patent application No. 201910498353.1, mailed on Mar. 30, 2021, with EN translation provided by Global Dossier.

Second Office Action for Chinese patent application No. 201910498353.1, mailed on Apr. 6, 2022 with EN translation provided by Global Dossier.

Extended European Search Report for European Patent Application 20822972.4, issued on Jul. 12, 2022.

Written Opinion for International Application PCT/CN2020/088645 issued Aug. 13, 2020 and its English Translation provided by WIPO.

International Preliminary Report on Patentability for International Application PCT/CN2020/088645 issued on Dec. 14, 2021.

* cited by examiner

HYPOGLYCEMIC PHARMACEUTICAL COMPOSITION

CROSS-REFERENCE TO RELATED APPLICATIONS

The present application is the U.S. national phase of PCT Application No. PCT/CN2020/088645 filed on May 6, 2020, which claims a priority to the Chinese patent application No. 201910498353.1 filed on Jun. 10, 2019, the disclosures of which are incorporated herein by reference in their entireties.

TECHNICAL FIELD

The invention relates to the technical field of biopharmaceutics, and specifically relates to a hypoglycemic pharmaceutical composition.

BACKGROUND ART

With the rapid economic growth and improvement in people's quality of life in China, the incidence of diabetes has also been increasing. According to the World Health Organization's report on the global status of non-communicable diseases, type 2 diabetes is now the third most threatening non-communicable disease to human health and life, ranked after cardiovascular diseases and tumors. Diabetes, as an independent risk factor, greatly increases the morbidity and mortality of cardiovascular diseases. Prevention and treatment of cardiovascular complications in patients with type 2 diabetes would significantly lower the risk of adverse cardiovascular events and improve the short- and long-term prognosis. The pathogenesis of diabetic cardiovascular diseases is complicated: hyperglycemia may cause disorders in the internal environment, leading to a hyperinsulinemic state, activating the neuroendocrine stress response system, and in turn incurring a series of cardiovascular diseases, such as hypertension, coronary heart disease, stroke, heart failure, chronic kidney disease, etc.

Glucagon-like peptide-1 (GLP-1) is a gastrointestinal hormone secreted by the L cells in the distal part of the colon and small intestine, and can stimulate the pancreas to secrete insulin to exert its main function in lowering the blood sugar. GLP-1 receptor agonists are homologues (97%) of GLP-1, more effective than GLP-1 and not rapidly degradable by dipeptidyl peptidase-4 (DDP-4) in vivo, and further elevate the level of GLP-1 by binding to the GLP-1 receptor, so as to replace GLP-1 and produce a physiologically required drug concentration. Several studies have shown that GLP-1 receptor agonists have the advantages of reducing the body weight, restoring the islet β-cell function and producing less hypoglycemia, and thus are increasingly used in clinical scenarios, for example, Exenatide and Liraglutide. Recent domestic and abroad studies have shown that in addition to the significant hypoglycemic effect, GLP-1 receptor agonists can also exert an anti-atherosclerotic effect by promoting vasodilatation, controlling inflammation, inhibiting monocyte adhesion, and inhibiting smooth muscle cell proliferation, thereby improving occurrence and development of cardiovascular complications in patients with type 2 diabetes. Type 2 diabetes patients are at a high risk of having cardiovascular diseases. Prevention and treatment of cardiovascular complications is an important aspect in the treatment of diabetes and can significantly improve the short- and long-term prognosis of patients with type 2 diabetes. With their unique, efficient and safe mechanism of action, GLP-1 receptor agonists offer cardiovascular protection for patients with type 2 diabetes by lowering the blood sugar, blood pressure, and blood lipids, controlling the body weight, improving vascular endothelial functions, protecting myocardium, and improving cardiac diastolic and systolic functions. At present, many clinical trials on the efficacy and safety of GLP-1 receptor agonists for treatment of cardiovascular complications in diabetes are ongoing on larger scales. We believe that in the near future GLP-1 receptor agonists would become an important treatment strategy against cardiovascular complications in diabetes.

The GLP-1 agonists currently available in the market are all injections of polypeptides, which are disadvantageous in that they are inconvenient for diabetic patients to use and cause pain. Therefore, it is of great significance to change the route of administration of GLP-1 agonists.

SUMMARY OF INVENTION

For the above reasons, the applicant conducted extensive creative studies and discovered a novel composition for promoting small-intestinal absorption, the composition comprising sodium lauryl sulfate, carbomer, chitosan, and sodium citrate. Studies demonstrated that the composition for promoting small intestinal absorption according to the present invention may be prepared into a composite adjuvant, which, when combined with a GLP-1 agonist, can improve the absorption of this active ingredient in the small intestine and the like.

The present invention is achieved through the following technical solutions.

Provided is a pharmaceutical composition having a hypoglycemic effect, comprising: a GLP-1 receptor agonist, and a composition for promoting small-intestinal absorption; wherein the composition for promoting small-intestinal absorption comprises sodium lauryl sulfate, carbomer, chitosan, and sodium citrate.

Preferably, the pharmaceutical composition is prepared into an oral formulation.

The GLP-1 receptor agonist includes: Exenatide, Liraglutide, Lixisenatide, Semaglutide, Benaglutide, Pramlintide, and the like.

The composition for promoting small-intestinal absorption may be used to ensure absorption of GLP-1 receptor agonists in the small intestine.

The composition for promoting small-intestinal absorption may be used to promote absorption of GLP-1 receptor agonists in the small intestine.

Therein the sodium lauryl sulfate, carbomer, chitosan, and sodium citrate may be in a weight ratio of 15-25:5-8:5-8:50-80.

Therein the GLP-1 receptor agonist and the composition for promoting small-intestinal absorption may be in a weight ratio of 1:5-860.

Also provided is an oral formulation having a hypoglycemic effect, comprising: a GLP-1 receptor agonist, sodium lauryl sulfate, carbomer, chitosan, and sodium citrate.

Therein the sodium lauryl sulfate, carbomer, chitosan, and sodium citrate may be in a weight ratio of 15-25:5-8:5-8:50-80.

Therein the GLP-1 receptor agonist and the composition for promoting small-intestinal absorption may be in a weight ratio of 1:5-860.

Also provided is a pharmaceutical composition having a hypoglycemic effect, prepared from raw materials comprising a GLP-1 receptor agonist and a composition for promoting small-intestinal absorption; wherein the composition for promoting small-intestinal absorption comprises sodium lauryl sulfate, carbomer, chitosan, and sodium citrate.

The composition for promoting small-intestinal absorption according to the present invention is a novel adjuvant that enables oral administration of drugs (effective ingredients or active ingredients) which were previously for injection only and not for oral administration, thereby changing the administration route of the drugs (effective ingredients or active ingredients).

The composition for promoting small-intestinal absorption according to the present invention can promote intestinal absorption of drugs (effective ingredients or active ingredients) that are easily decomposed in the gastrointestinal tract.

The composition for promoting small-intestinal absorption according to the present invention can promote intestinal absorption of drugs (effective ingredients or active ingredients) that are not easily absorbed in the gastrointestinal tract.

Since the composition for promoting small-intestinal absorption according to the present invention promotes small-intestinal absorption of drugs (effective ingredients or active ingredients) which requires release of the drugs in the small intestine to perform its functions, in pharmacodynamic and pharmacokinetic tests, drugs were administered to rodents by a small-intestinal catheter, or to mammals orally in the form of enteric capsules.

In the present invention, the composition for promoting small-intestinal absorption was combined with individual drugs (effective ingredients or active ingredients) and tested for bioavailability in rodents, and meanwhile some polypeptides were selected for pharmacodynamic and pharmacokinetic tests on different animals.

BRIEF DESCRIPTION OF DRAWINGS

FIG. 1 shows the PD test with Exenatide in STZ rats, wherein the x axis is time (h), and the y axis is the hypoglycemic efficiency (%);
the solid circles with a solid line represent small-intestinal injection of normal saline at 2 ml/kg,
the solid squares with a dashed line represent subcutaneous injection of Exenatide at 1 µg/kg,
the solid circles with a dashed line represent subcutaneous injection of Exenatide at 250 µg/kg,
the solid triangles with a dashed line represent subcutaneous injection of Exenatide at 1 mg/kg,
the hollow triangles with a solid line represent small-intestinal administration of the composition of Example 1+ Exenatide (dose: Exenatide 30 µg/kg),
the hollow circles with a solid line represent small-intestinal administration of the composition of Example 1+ Exenatide (dose: Exenatide 40 µg/kg),
the hollow squares with a solid line represent small-intestinal administration of the composition of Example 1+ Exenatide (dose: Exenatide 50 µg/kg), and
the hollow rhombuses with a solid line represent small-intestinal administration of the composition of Example 1+ Exenatide (dose: Exenatide 60 µg/kg).

DETAILED DESCRIPTION OF INVENTION

The following specific examples are given to illustrate technical solutions of the present invention, but the scope of protection of the present invention is not limited thereto.

The examples shown in this specification only exemplify the embodiments of the inventive concept. The scope of protection of the present invention should not be construed as limited to the specific forms described in the examples, but should also be extended to equivalent technical means conceivable by a person skilled in the art based on the idea of the present invention. Although some embodiments of the present invention are described below, the present invention is not limited to these embodiments or the field they are applied to. The following embodiments are merely illustrative, instructive, and not restrictive.

The following experiments according to the present invention are conclusive experiments conducted by the inventors based on many creative experiments, representing the technical solutions of the present invention to be claimed. The quantitative tests in the following Examples are all from triplicate experiments, and the data is given as the average or the average±standard deviation of the triplicate experiments.

Example 1

Significant Improvement in Efficacy of Exenatide (Exendin4, EXE4) after Small-Intestinal Administration The composition for promoting small-intestinal absorption: sodium lauryl sulfate, carbomer, chitosan, and sodium citrate, in a weight ratio of 20:6.5:6.5:65.

Exenatide and the above composition were mixed thoroughly in a weight ratio of 1:5, and reserved for further use.

Laboratory animals: SD male rats, intraperitoneally injected with 45 mg/kg STZ to establish a hyperglycemia model.

Small intestine efficacy test: administration was through subcutaneous injection (sc) or a small-intestine catheter (ei), and blood samples were collected at 0 h, 3 h, 6 h and 9 h to measure the blood sugar.

Figure 1:
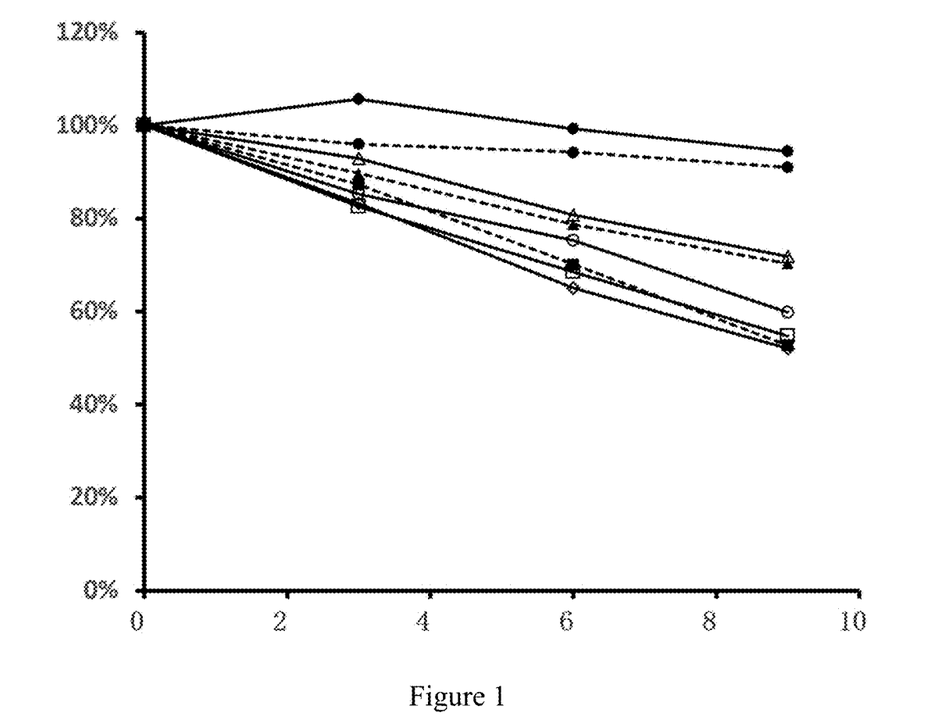

The results show that, in the absence of the composition described above, Exenatide after small-intestine administration showed a very weak hypoglycemic effect. When its dose reached 1 mg/kg, the hypoglycemic efficiency after 9 h was merely about 70%, far lower than the hypoglycemic efficiency of about 50% achieved by its subcutaneous dose of 1 µg/kg. However, after addition of the composition of the present invention, a dose of 50 µg/kg can achieve the hypoglycemic effect achieved by a subcutaneous dose of 1 µg/kg. See FIG. 1.

Example 2

Significant Improvement in Bioavailability of Exenatide after Small-Intestinal Administration Exenatide and the composition for promoting small-intestinal absorption of Example 1 were mixed thoroughly in a weight ratio of 1:5, and reserved for further use.

Laboratory animals: adult male SD rats.

PK test for small-intestinal administration: Exenatide was administered to fasted adult SD rats in a volume of 1 ml/kg via a small-intestine catheter, such that the dose of Exenatide was 200 µg/kg. In another group, Exenatide at 200 µg/kg either alone or together with the composition of the present invention was administered via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

Figure 2:
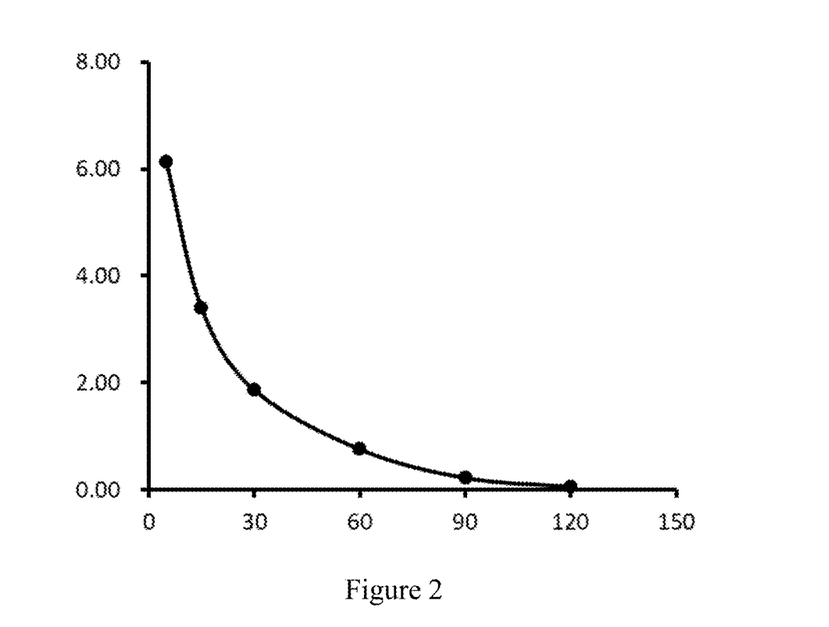
FIG. 2 shows the iv PK test with Exenatide in rats; wherein the x axis is time (h), and the y axis is the plasma concentration of Exenatide in rats (ng/ml).
Figure 3:
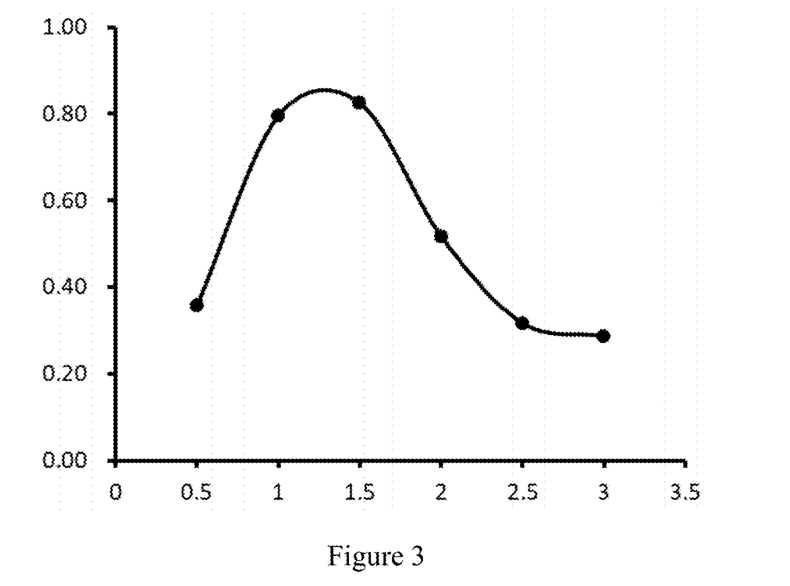
FIG. 3 shows the ei PK test with Exenatide/the composition of Example 1 in rats; wherein the x axis is time (h), and the y axis is the plasma concentration of Exenatide in rats (ng/ml).

The results showed that the AUC in the PK curve for 1 µg/kg i.v. injected Exenatide was 0.93 ng/ml.h, while the blood concentration after the small-intestinal injection of 200 µg/kg was lower than the detection limit of ELISA. After addition of the composition of Example 1, the AUC in the PK curve could reach 1.47 ng/ml.h, and the bioavailability of small-intestinal administration was about 0.79%. The test results are shown in FIG. 2 and FIG. 3.

Example 3

Significant Improvement in Oral Bioavailability of Exenatide 0.7 mg of Exenatide was mixed thoroughly with 200 mg of the composition for promoting small-intestinal absorption of Example 1, freeze-dried, loaded into a #3 enteric capsule, and reserved for further use;

0.7 mg of Exenatide was mixed thoroughly with 400 mg of the composition for promoting small-intestinal absorption of Example 1, freeze-dried, loaded into a #0 enteric capsule, and reserved for further use;

0.7 mg of Exenatide was mixed thoroughly with 600 mg of the composition for promoting small-intestinal absorption of Example 1, freeze-dried, loaded into a #00 enteric capsule, and reserved for further use;

0.7 mg of Exenatide was mixed thoroughly with 200 mg of the composition for promoting small-intestinal absorption of Example 1, freeze-dried, loaded into a #3 normal capsule, and reserved for further use;

0.7 mg of Exenatide was mixed thoroughly with 200 mg of mannitol, freeze-dried, loaded into a #3 enteric capsule, and reserved for further use.

Laboratory animals: adult male beagle dogs.

PK test for oral administration: The enteric capsules were orally administered to fasted animals, and then blood samples were collected after 0.5, 1, 1.5, 2, 2.5, and 3 h. The blood samples were anticoagulated with 10 mM EDTA, and centrifuged at 4° C. at 3000 rpm for 5 min. Plasma was collected and subjected to quick freezing.

Figure 4:
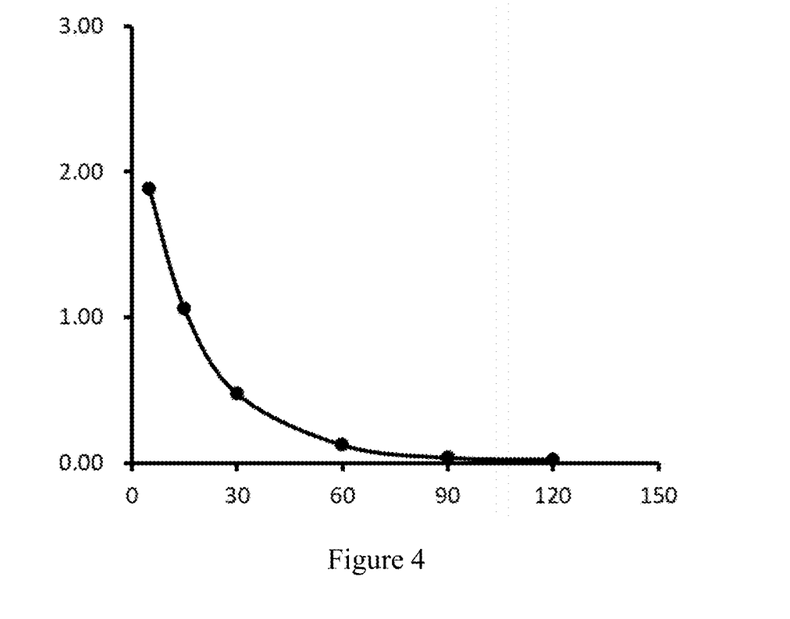
FIG. 4 shows the iv PK test with Exenatide in beagle dogs; wherein the x axis is time (h), and the y axis is the plasma concentration of Exenatide in beagle dogs (ng/ml).
Figure 5:
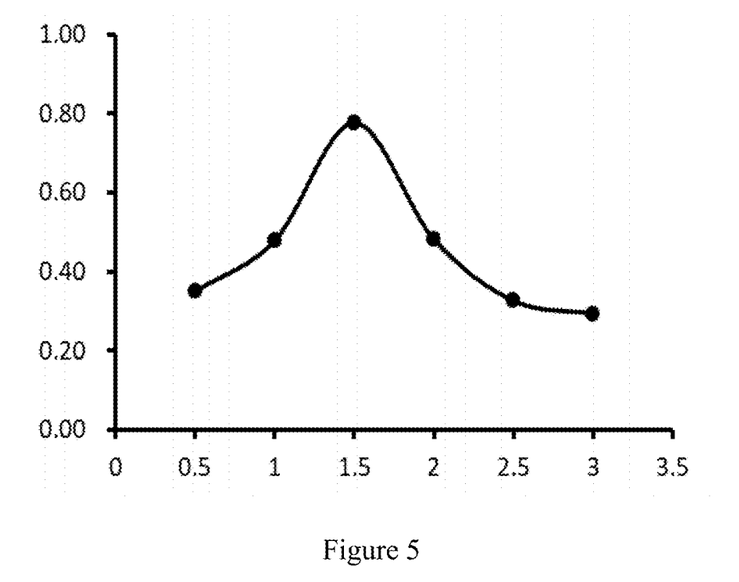
FIG. 5 shows the po PK test with Exenatide/the composition of Example 1 in beagle dogs; wherein the x axis is time (h), and the y axis is the plasma concentration of Exenatide in beagle dogs (ng/ml).

PK test for intravenous administration: Exenatide was injected intravenously to fasted animals at 0.3 µg/kg, and then blood samples were collected after 5, 15, 30, 60, 90, and 120 min. The blood samples were anticoagulated with 10 mM EDTA, and centrifuged at 4° C. at 3000 rpm for 5 min. Plasma was collected and subjected to quick freezing. See FIG. 4 and FIG. 5.

In order to avoid hypoglycemia in animals, 1 g/kg glucose was given before administration. ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The PK data for beagle dogs show that the AUC of 0.3 µg/kg intravenously injected Exenatide was about 0.82 ng/ml.h, and the AUC of 0.7 mg orally administered Exenatide/the composition of Example 1 was about 1.36 ng/ml.h. The bioavailability of orally administered Exenatide/Composition of Example 1 was about 0.83%.

Without the assistance of the composition of the present invention, Exenatide cannot successfully enter the blood. After addition of the composition of the present invention, the efficiency of entering the blood was significantly improved. As the weight of the composition of Example 1 increased, the efficiency of Exenatide entering the blood also slightly increased, but to a limited degree. Considering convenience of oral administration and effectiveness of drugs, the dose of #3 capsules was more appropriate.

TABLE 1 po PD tests on beagle dogs with Exenatide/Composition
for promoting small-intestinal absorption of Example 1

| Drug | Adjuvant | Capsules | 0.5 h | 1.0 h | 1.5 h | 2.0 h | 2.5 h | 3.0 h | AUC ng/ml · h |
|---|---|---|---|---|---|---|---|---|---|
| Exenatide 0.7 mg | Composition of Example 1 200 mg | #3 Enteric | 0.350 | 0.479 | 0.777 | 0.482 | 0.326 | 0.294 | 1.281 |
| Exenatide 0.7 mg | Composition of Example 1 400 mg | #0 Enteric | 0.319 | 0.442 | 0.814 | 0.482 | 0.290 | 0.268 | 1.240 |
| Exenatide 0.7 mg | Composition of Example 1 600 mg | #00 Enteric | 0.364 | 0.549 | 0.893 | 0.510 | 0.380 | 0.313 | 1.426 |
| Exenatide 0.7 mg | Composition of Example 1 200 mg | #3 Normal | (0.032) | 0.013 | (0.055) | 0.024 | (0.026) | (0.021) | — |
| Exenatide 0.7 mg | Mannitol 200 mg | #3 Enteric | (0.026) | (0.021) | 0.007 | (0.049) | (0.132) | (0.037) | — |

Example 4

Exenatide/Composition for Promoting Small-Intestinal Absorption of Example 1 can Significantly Inhibit the Increase in Postprandial Blood Sugar of Alloxan Beagle Dogs 0.7 mg of Exenatide was mixed thoroughly with 200 mg of the composition for promoting small-intestinal absorption of Example 1, freeze-dried, loaded into a #3 enteric capsule, and reserved for further use.

Laboratory animals: adult male beagle dogs.

Physical examination and adaptation of animals: Blood samples from fasted animals were collected to test blood biochemical indicators. Once everything was confirmed normal, the animals were placed in a quiet room to adapt for 1 week. The daily feeding time and feeding amount were required to be consistent.

Data collection before modeling: Blood samples were collected at 4 time points every day (before feeding, and 2 h, 4 h, 6 h after feeding) for 5 consecutive days.

Modeling: an Alloxan solution was intravenously injected at 60 mg/kg to fasted animals. One week later, blood samples were collected at 4 time points every day (before feeding, and 2 h, 4 h, 6 h after feeding) for 5 consecutive days. Qualification of the model was evaluated based on the collected data. If the model was qualified, the efficacy test was started.

Efficacy test: Animals swallowed the test capsules before feeding, and blood samples were collected at 4 time points (before feeding, and 2 h, 4 h, 6 h after feeding).

Figure 6:
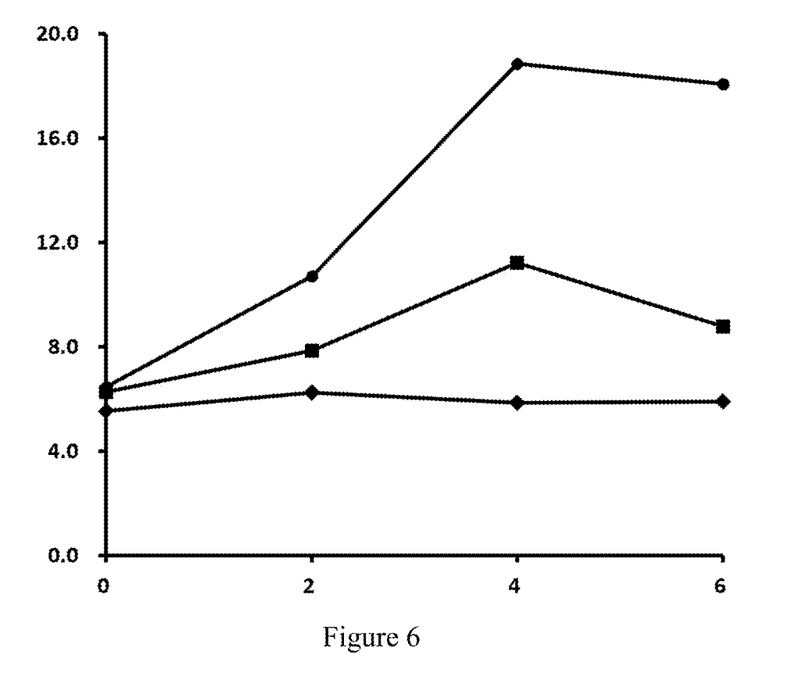
FIG. 6 shows the PD test with Exenatide in Alloxan beagle dogs; wherein the x axis is time (h), and the y axis is the blood sugar (mM) in beagle dogs;
the solid circles with a solid line are the postprandial blood sugar of Alloxan beagle dogs, the solid squares with a solid line are the postprandial blood sugar of Alloxan beagle dogs after swallowing Exenatide/the composition of Example 1, and the solid rhombuses with a solid line are the postprandial blood sugar of normal beagle dogs.

The results show that the Exenatide/the composition for promoting small-intestinal absorption of Example 1 can significantly inhibit the increase in postprandial blood sugar of Alloxan-modelled beagle dogs. See FIG. 6.

Conclusion: The above experiment demonstrates that the composition for promoting small-intestinal absorption according to the present invention can effectively promote intestinal absorption of active ingredients that were previously not for oral administration, and can be used as a novel pharmaceutical adjuvant.

Example 5

The Composition for Promoting Small-Intestinal Absorption According to the Present Invention Significantly Improves the Bioavailability of Liraglutide after Small-Intestinal Administration The composition for promoting small-intestinal absorption of the present invention: sodium lauryl sulfate, carbomer, chitosan, and sodium citrate, in a weight ratio of 20:6.5:6.5:65.

Liraglutide and the composition for promoting small-intestinal absorption according to the present invention were mixed thoroughly in a weight ratio of 1:5, and reserved for further use.

Laboratory animals: adult male SD rats.

PK test for small-intestinal administration: Liraglutide was administered to fasted adult SD rats in a volume of 1 ml/kg via a small-intestine catheter, such that the dose of Liraglutide was 200 μg/kg. In another group, Liraglutide at 200 μg/kg either alone or together with the composition for promoting small-intestinal absorption according to the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Liraglutide after the small-intestinal injection at 200 μg/kg was lower than the detection limit of ELISA. After addition of the composition for promoting small-intestinal absorption according to the present invention, the bioavailability of small-intestinal administration was about 0.57%.

Example 6

The Composition for Promoting Small-Intestinal Absorption According to the Present Invention Significantly Improves the Bioavailability of Lixisenatide after Small-Intestinal Administration The composition for promoting small-intestinal absorption of the present invention: sodium lauryl sulfate, carbomer, chitosan, and sodium citrate, in a weight ratio of 20:6.5:6.5:65.

Lixisenatide and the composition for promoting small-intestinal absorption according to the present invention were mixed thoroughly in a weight ratio of 1:5, and reserved for further use.

Laboratory animals: adult male SD rats.

PK test for small-intestinal administration: Lixisenatide was administered to fasted adult SD rats in a volume of 1 ml/kg via a small-intestine catheter, such that the dose of Lixisenatide was 200 μg/kg. In another group, Lixisenatide at 200 μg/kg either alone or together with the composition for promoting small-intestinal absorption according to the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Lixisenatide after the small-intestinal injection at 200 μg/kg was lower than the detection limit of ELISA. After addition of the composition for promoting small-intestinal absorption according to the present invention, the bioavailability of small-intestinal administration was about 0.44%.

Example 7

The Composition for Promoting Small-Intestinal Absorption According to the Present Invention Significantly Improves the Bioavailability of Benaglutide after Small-Intestinal Administration The composition for promoting small-intestinal absorption of the present invention: sodium lauryl sulfate, carbomer, chitosan, and sodium citrate, in a weight ratio of 20:6.5:6.5:65.

Benaglutide and the composition for promoting small-intestinal absorption according to the present invention were mixed thoroughly in a weight ratio of 1:5, and reserved for further use.

Laboratory animals: adult male SD rats.

PK test for small-intestinal administration: Benaglutide was administered to fasted adult SD rats in a volume of 1 ml/kg via a small-intestine catheter, such that the dose of Benaglutide was 200 μg/kg. In another group, Benaglutide at 200 μg/kg either alone or together with the composition for promoting small-intestinal absorption according to the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Benaglutide after the small-intestinal injection at 200 μg/kg was lower than the detection limit of ELISA. After addition of the composition for promoting small-intestinal absorption according to the present invention, the bioavailability of small-intestinal administration was about 0.70%.

Example 8

The Composition for Promoting Small-Intestinal Absorption According to the Present Invention Significantly Improves the Bioavailability of Semaglutide after Small-Intestinal Administration The composition for promoting small-intestinal absorption of the present invention: sodium lauryl sulfate, carbomer, chitosan, and sodium citrate, in a weight ratio of 20:6.5:6.5:65.

Semaglutide and the composition for promoting small-intestinal absorption according to the present invention were mixed thoroughly in a weight ratio of 1:5, and reserved for further use.

Laboratory animals: adult male SD rats.

PK test for small-intestinal administration: Semaglutide was administered to fasted adult SD rats in a volume of 1 ml/kg via a small-intestine catheter, such that the dose of Semaglutide was 200 μg/kg. In another group, Semaglutide at 200 μg/kg either alone or together with the composition for promoting small-intestinal absorption according to the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

In order to avoid hypoglycemia in the animals, 1 g/kg glucose was given before administration.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Semaglutide after the small-intestinal injection at 200 μg/kg was lower than the detection limit of ELISA. After addition of the composition for promoting small-intestinal absorption according to the present invention, the bioavailability of small-intestinal administration was about 0.32%.

Example 9

The Composition According to the Present Invention Significantly Improves Bioavailability of Pramlintide after Small-Intestinal Administration The composition for promoting small-intestinal absorption according to the present invention: sodium lauryl sulfate, carbomer, chitosan, and sodium citrate, in a weight ratio of 20:6.5:6.5:65.

Pramlintide and the composition for promoting small-intestinal absorption of the present invention were mixed thoroughly in a weight ratio of 1:5, and reserved for further use.

Laboratory animals: adult male SD rats.

PK test for small-intestinal administration: Pramlintide was administered to fasted adult SD rats in a volume of 1 ml/kg via a small-intestine catheter, such that the dose of Pramlintide was 200 μg/kg. In another group, Pramlintide at 200 μg/kg together with the composition for promoting small-intestinal absorption of the present invention was injected via a small-intestine catheter (ei), and blood samples were collected from tail vein at 0 h, 0.5 h, 1 h, 1.5 h, 2 h, 2.5 h and 3 h after administration. The blood samples were anticoagulated with 10 mM EDTA and centrifuged at 4° C. at 3000 rpm for 5 min. The plasma was collected and subjected to quick freezing.

PK test for intravenous administration: Pramlintide was intravenously injected to fasted animals at 1 μg/kg, and blood samples were collected at 5, 15, 30, 60, 90 and 120 min. The blood samples were anticoagulated with 10 mM EDTA and centrifuged at 4° C. at 3000 rpm for 5 min. The plasma was collected and subjected to quick freezing.

ELISA assay: Coating with a mouse monoclonal antibody against the target polypeptide, blocking with 1% BSA, incubating with a blood sample or a standard diluted with 0.1% BSA, capturing with Biotin-labeled rabbit polyclonal antibody against the target polypeptide, incubating with HRP-conjugated strepavidin, then developing with TMB, which was stopped with HCl, and reading at 450 nm. A standard curve was obtained from standards, and the concentration of the target polypeptide in the plasma was calculated.

AUC was calculated based on the PK curve, and the bioavailability of small-intestinal administration was calculated with respect to 100% of the bioavailability of intravenous injection (iv).

The results showed that the blood concentration of Pramlintide after the small-intestinal administration at 200 μg/kg was lower than the detection limit of ELISA. After addition of the composition for promoting small-intestinal absorption of the present invention, the bioavailability of small-intestinal administration could reach 1.77%.

Under the enlightenment of the specification, a person ordinarily skilled in the art can make many further embodiments that all fall within the scope of protection of the present invention, without departing from the scope of the claims of the present invention.

What is claimed is:

1. A pharmaceutical composition having a hypoglycemic effect, consisting of: a GLP-1 receptor agonist, and a composition for promoting small-intestinal absorption; wherein the composition for promoting small-intestinal absorption consists of sodium lauryl sulfate, carbomer, chitosan, and sodium citrate.

2. The pharmaceutical composition having a hypoglycemic effect according to claim 1, wherein the GLP-1 receptor agonist is: Exenatide, Liraglutide, Lixisenatide, Dulaglutide, Benaglutide, Semaglutide, Pramlintide or Albiglutide.

3. The pharmaceutical composition having a hypoglycemic effect according to claim 1, wherein the sodium lauryl sulfate, carbomer, chitosan, and sodium citrate are in a weight ratio of 15-25:5-8:5-8:50-80, respectively.

4. The pharmaceutical composition having a hypoglycemic effect according to claim 1, wherein the GLP-1 receptor agonist and the composition for promoting small-intestinal absorption are in a weight ratio of 1:5-860, respectively.

5. A pharmaceutical composition having a hypoglycemic effect, consisting of a GLP-1 receptor agonist, and a composition for promoting small-intestinal absorption; wherein
the GLP-1 receptor agonist is Exenatide, Liraglutide, Lixisenatide, Benaglutide, Semaglutide or Pramlintide;
the composition for promoting small-intestinal absorption consists of sodium lauryl sulfate, carbomer, chitosan, and sodium citrate, wherein the sodium lauryl sulfate, carbomer, chitosan, and sodium citrate are in a weight ratio of 20:6.5:6.5:65, respectively; and
the GLP-1 receptor agonist and the composition for promoting small-intestinal absorption are in a weight ratio of 1:5, respectively.

6. The pharmaceutical composition having the hypoglycemic effect according to claim 1, wherein the sodium lauryl sulfate, carbomer, chitosan, and sodium citrate are in a weight ratio of 20:6.5:6.5:65, respectively.

7. The pharmaceutical composition having a hypoglycemic effect according to claim 1, wherein the GLP-1 receptor agonist and the composition for promoting small-intestinal absorption are in a weight ratio of 1:5, respectively.

* * * * *